(12) United States Patent
Schüssler et al.

(10) Patent No.: US 8,101,275 B2
(45) Date of Patent: Jan. 24, 2012

(54) DEVICE BASED ON NITINOL, A PROCESS FOR ITS PRODUCTION, AND ITS USE

(75) Inventors: Andreas Schüssler, Pfinztal (DE);
Michael Grunze, Neckargemünd (DE);
Roman Denk, Weidenstetten (DE)

(73) Assignee: Celonova Biosciences, Inc., San Antonio, TX (US)

( * ) Notice: Subject to any disclaimer, the term of this patent is extended or adjusted under 35 U.S.C. 154(b) by 0 days.

(21) Appl. No.: 11/725,709

(22) Filed: Mar. 19, 2007

(65) Prior Publication Data
US 2007/0184277 A1    Aug. 9, 2007

(30) Foreign Application Priority Data

Aug. 17, 2001 (DE) ................................ 101 40 522
Jan. 23, 2002 (DE) ................................ 102 02 467

(51) Int. Cl.
*B32B 15/08* (2006.01)
*A61F 2/82* (2006.01)
(52) U.S. Cl. ........ 428/421; 428/457; 428/469; 428/472; 428/472.1; 427/2.1; 427/2.24; 623/1.18
(58) Field of Classification Search .................. None
See application file for complete search history.

(56) References Cited

U.S. PATENT DOCUMENTS

| | | |
|---|---|---|
| 4,311,736 A | 1/1982 | Leong |
| 4,318,947 A | 3/1982 | Joung |
| 4,341,844 A | 7/1982 | Leong |
| 4,424,395 A | 1/1984 | Strom |
| 4,451,647 A | 5/1984 | Allcock et al. |
| 4,480,642 A | 11/1984 | Stoy et al. |
| 4,579,880 A | 4/1986 | Ohashi |
| 4,592,755 A | 6/1986 | Pettigrew et al. |
| 4,798,876 A | 1/1989 | Gould et al. |
| 4,880,622 A | 11/1989 | Allcock et al. |
| 4,883,699 A | 11/1989 | Aniuk et al. |
| 4,911,691 A | 3/1990 | Aniuk et al. |
| 4,975,280 A | 12/1990 | Schacht et al. |
| 5,238,569 A | 8/1993 | Soria et al. |
| 5,439,446 A | 8/1995 | Barry |
| 5,548,060 A | 8/1996 | Allcock et al. |
| 5,552,159 A | 9/1996 | Mueller et al. |
| 5,605,696 A | 2/1997 | Eury et al. |
| 5,634,946 A | 6/1997 | Slepian |
| 5,707,597 A | 1/1998 | Andrianov et al. |
| 5,716,981 A | 2/1998 | Hunter et al. |
| 5,788,979 A | 8/1998 | Alt et al. |
| 5,814,704 A | 9/1998 | Andrianov et al. |
| 5,873,904 A | 2/1999 | Ragheb et al. |
| 5,886,026 A | 3/1999 | Hunter et al. |
| 5,914,388 A | 6/1999 | Allcock |
| 5,980,972 A | 11/1999 | Ding |
| 5,997,301 A | 12/1999 | Linden |
| 6,007,573 A | 12/1999 | Wallace et al. |
| 6,077,916 A | 6/2000 | Laurencin |
| 6,254,634 B1 | 7/2001 | Anderson |
| 6,273,913 B1 | 8/2001 | Wright et al. |
| 6,299,604 B1 * | 10/2001 | Ragheb et al. ................. 604/265 |
| 6,319,984 B1 | 11/2001 | Song et al. |
| 6,346,110 B2 | 2/2002 | Wu |
| 6,432,128 B1 | 8/2002 | Wallace et al. |
| 6,485,514 B1 | 11/2002 | Wrenn, Jr. |
| 6,503,556 B2 | 1/2003 | Harish et al. |
| 6,506,411 B2 | 1/2003 | Hunter et al. |
| 6,569,195 B2 | 5/2003 | Yang et al. |
| 6,626,937 B1 * | 9/2003 | Cox ............................. 623/1.18 |
| 6,652,575 B2 | 11/2003 | Wang |
| 6,669,719 B2 | 12/2003 | Wallace et al. |
| 2001/0014717 A1 | 8/2001 | Hossainy et al. |
| 2001/0029351 A1 | 10/2001 | Faletico et al. |
| 2002/0005206 A1 | 1/2002 | Faletico et al. |
| 2002/0051730 A1 | 5/2002 | Bodnar et al. |
| 2002/0094440 A1 | 7/2002 | Llanos et al. |
| 2002/0111590 A1 | 8/2002 | Davila et al. |
| 2002/0119202 A1 | 8/2002 | Hunter et al. |
| 2002/0133183 A1 | 9/2002 | Lentz et al. |
| 2002/0143386 A1 | 10/2002 | Davila et al. |
| 2002/0165608 A1 | 11/2002 | Llanos et al. |
| 2003/0004568 A1 | 1/2003 | Ken et al. |
| 2003/0060877 A1 | 3/2003 | Falotico et al. |
| 2003/0065345 A1 | 4/2003 | Weadock |
| 2003/0065377 A1 | 4/2003 | Davila et al. |
| 2003/0153983 A1 | 8/2003 | Miller et al. |
| 2003/0176915 A1 | 9/2003 | Wright et al. |
| 2003/0204168 A1 | 10/2003 | Bosma et al. |
| 2004/0059373 A1 | 3/2004 | Shapiro et al. |
| 2004/0117001 A1 * | 6/2004 | Pelton et al. ................. 623/1.15 |

FOREIGN PATENT DOCUMENTS

| | | |
|---|---|---|
| CA | 1 252 253 | 5/1986 |
| DE | 196 13 048 C2 | 10/1996 |
| DE | 100 19 982 A | 10/2001 |
| DE | 101 00 961 A1 | 8/2002 |
| EP | 0 150 699 A2 | 8/1985 |

(Continued)

OTHER PUBLICATIONS

A. Welle et al. Blood Compatibility of Poly[bis(trifluoroethoxy)phosphazene], Institute of Applied Physical Chemistry, JAMP, vol. 4, 6-10 (2000), University of Heidelberg, Germany.

(Continued)

*Primary Examiner* — Monique Jackson
(74) *Attorney, Agent, or Firm* — Rissman Hendricks & Oliverio LLP

(57) ABSTRACT

The present invention relates to a device comprising a substrate based essentially on nitinol and, arranged thereon at least partially, a covering or a coating based on at least one polyphosphazene derivative having the general formula (I), a process for its production, and the use of the device as an artificial implant, vascular or nonvascular stent, catheter, thrombolectomy or embolectomy catheter, fragmentation spindle or catheter, filter, vascular connector, hernia patch, oral, dental or throat implant or urether.

26 Claims, No Drawings

FOREIGN PATENT DOCUMENTS

| | | |
|---|---|---|
| EP | 0 286 709 A1 | 10/1988 |
| EP | 0 804 909 A2 | 11/1997 |
| EP | 0 970 711 B1 | 1/2000 |
| EP | 1 112 094 B1 | 7/2001 |
| EP | 1 179 353 A1 | 2/2002 |
| JP | 58-079915 A | 5/1983 |
| WO | WO 93/21858 A1 | 11/1993 |
| WO | WO 95/02628 A1 | 1/1995 |
| WO | WO 96/00103 A1 | 1/1996 |
| WO | WO 96/04015 A1 | 2/1996 |
| WO | WO 96/25176 A1 | 8/1996 |
| WO | WO 96/25897 A2 | 8/1996 |
| WO | WO 98/43618 A2 | 10/1998 |
| WO | WO 98/52605 A1 | 11/1998 |
| WO | WO 98/56312 A1 | 12/1998 |
| WO | WO 99/09088 A | 2/1999 |
| WO | WO 99/16416 A2 | 4/1999 |
| WO | WO 99/16477 A2 | 4/1999 |
| WO | WO 99/42147 A1 | 8/1999 |
| WO | WO 00/32238 | 6/2000 |
| WO | WO 01/87372 A1 | 4/2001 |
| WO | WO 01/36008 A3 | 5/2001 |
| WO | WO 01/45763 A1 | 6/2001 |
| WO | WO 01/49340 A1 | 7/2001 |
| WO | WO 01/70296 A1 | 9/2001 |
| WO | WO 01/80919 A1 | 11/2001 |
| WO | WO 01/87368 A1 | 11/2001 |
| WO | WO 02/24247 A1 | 3/2002 |
| WO | WO 2004/004795 A1 | 1/2004 |
| WO | WO 2004/011055 A2 | 2/2004 |

OTHER PUBLICATIONS

A. Welle et al., "Polyphosphazenes as Antithrombotic Coatings for Prosthetic Heart Valves," Presented at 19 Annual Meeting of the Adhesion Society, Myrtle Beach, SC, 4 pages (Feb. 1996).

C. Herzog et al., "Peripheral Artery Stent Visualization and In-stent Stenosis Analysis in 16-Row Computed Tomography: an In-vitro Evaluation," Eur Radiol, vol. 15, 2276-2283 (2005).

C.T. Laurencin et al., "Use of polyphosphazenes for skeletal tissue regeneration," J. Biomedical Materials Research, vol. 27, No. 7, pp. 963-973 (1993), John Wiley & Sons, Inc., USA.

D.Y. Sze, MD, Ph.D., et al., "The Y Stent: A Technique Using Nitinol Stents to Treat Bifurcations," J. of Endovascular Therapy, vol. 10: 780-787, 2003.

F. Veronese et al., "Polyphosphazene Membranes and Microspheres in Periodontal Diseases and Implant Surgery," Biomaterials, vol. 20, 91-98 (1999), Elsevier, USA.

G. Lopez et al., "Glow Discharge Plasma Deposition of Tetraethylene Glycol Dimethyl Ether for Fouling-Resistant Biomaterial Surfaces," J. of Biomedical Materials Research, vol. 26, 415-439 (1992), John Wiley & Sons, Inc., USA.

H. Allcock et al., "Antibacterial activity and mutagenicity studies of water-soluble phosphazene high polymers," Biomaterials, vol. 13, No. 2, pp. 847-862 (1992), Butterworth-Heinemann Ltd., USA.

H. Allcock, "Polyphosphazenes," Inorganic Polymers, pp. 61-139 (1992).

I. De Scheerder et al., "Angiopeptin Loaded Stents Inhibit the Neointimal Reaction Induced by Polymer Coated Stents Implanted in Porcine Coronary Arteries," Abstract 772-6, pp. 286A, JACC (Feb. 1995).

J. Ruef et al., "Endovacular Interventions in Iliac and Infrainguinal Occlusive Artery Disease," Journal of Interventional Cardiology, vol. 17, 427-435 (Nov. 2004).

J. Ryhänen et al., "In vivo Biocompatibility Evaluation of Nickel-Titanium Shape Memory Metal Alloy; Muscle and Perineural Tissue Responses and Encapsule Membrane Thickness," J. Biomed Mater Res., vol. 41, 481-488 (1998).

J. Sindermann et al., "Biological Aspects of Radiation and Drug-Eluting Stents for the Prevention of Restenosis," Cardiovascular Research, vol. 63, 22-30 (2004), Elsevier, USA.

M. Gleria et al., "Fluorine Containing Phosphazene Polymers," J. of Fluorine Chemistry, vol. 125, 329-337 (2004), Elsevier, USA.

M. Gorbet & M. Sefton, "Biomaterial-Associated Thrombosis: Roles of Coagulation Factors, Complement, Platelets and Leukocytes," Biomaterials, vol. 25, 5681-5703 (2004), Elsevier, USA.

M. Kajiwara, "The Study of the Cultivation of Chinese Hamster Ovary and Bows Cell Lines," Phosphorus, Sulfur, and Silicon, vol. 76, pp. 163-166 (1993), Gordon and Breach Science Publishers S.A., USA.

P. Kingshott, "Surfaces that Resist Bioadhesion," Current Opinion in Solid State and Materials Science, vol. 4, 403-412 (1999), Pergamon.

Ph. Potin & R. DeJaeger, "Review: Polyphosphazenes: Synthesis, Structures, Properties, Applications," European Polymer Journal, vol. 27, 341-348 (1991), Pergamon Press, Great Britain.

R. De Jaeger & M. Gleria, "Poly(organophosphazene)s and Related Compounds: Synthesis, Properties and Applications," Prog. Polym. Sci., vol. 23, 179-276 (1998), Pergamon Press, Great Britain.

R. Waksman, "Vascular Brachytherapy: Applications in the Era of Drug-Eluting Stents," Reviews in Cardiovascular Medicine, vol. 3, S23-S30 (2002), MedReviews, LLC, USA.

R.R. McCaffrey et al., "Synthesis, Casting, and Diffusion Testing of Poly[bis(tri-fluoroethoxy)phosphazene] Membranes," J. of Membrane Science, vol. 28, 47-67 (1986), Elsevier Science Publishers B.V., Netherlands.

S. Cohen et al., "Design of Synthetic Polymeric Structures for Cell Transplantation and Tissue Engineering," Clinical Materials, vol. 13, 3-10 (1993), Elsevier Science Publishers Ltd, England.

S. H. Duda et al., "Endovascular Treatment of Peripheral Artery Disease with Expanded PTFE-Covered Nitinol Stents: Interim Analysis from a Perspective Controlled Study," CardioVascular and Interventional Radiology, vol. 25:413-418 (2002).

S. H. Duda et al., "Physical Properties of Endovascular Stents: An Experimental Comparison," Journal of Vascular and InterventionalRadiology, vol. 11 No. 5: 645-654, 2000.

S. Ibim et al., "Controlled Macromolecule Release from Poly(phosphazene) Matrices," J. of Controlled Release, vol. 40, 31-39 (Jun. 1996), Elsevier Science B.V. (Abstract).

S. Sabeti et al., "Primary Patency of Femoropopliteal Arteries Treated with Nitinol versus Stainless Steel Self-expanding Stents: Propensity Score—adjusted Analysis[1]," Radiololgy, vol. 232, No. 2, Aug. 2004.

S. Sabeti et al., "Primary Patency of Long-Segment Self-Expanding Nitinol Stents in the Femoropopliteal Arteries," J. of Endovascular Therapy, vol. 12, Jun. 12, 2005.

S. Sheth, MD, et al., "Subacute Thrombosis and Vascular injury Resulting from Slotted-Tube Nitinol and Stainless Steel Stents in a Rabbit Carotoid Artery Model," Circulation, vol. 94: 1733-1740, 1996.

S. Vinogradova et al., "Open-chain Poly(organophosphazenes). Synthesis and Properties," Russian Chemical Reviews, vol. 67, 515-534 (1998), Russian Academy of Sciences and Turpion Ltd.

V. Korsak et al., "On the Effect of Water on the Polymerization of Hexachlorocyclotriphosphazenes," Acta Polymerica, vol. 30, No. 5, 245-248 (1979).

W. Kellner, et al., "MR Imaging of Soft-Tissue Changes after Percutaneous Transluminal Angioplasty and Stent Placement," Radiology, vol. 202, 327-331 (1997).

Y. Lemmouchi et al., "Biodegradable Polyphosphazenes for Drug Delivery," Macromolecular Symposia, vol. 123, 103-112 (Sep. 1997) Wiley VCH, Weinheim, Germany.

\* cited by examiner

DEVICE BASED ON NITINOL, A PROCESS FOR ITS PRODUCTION, AND ITS USE

CROSS-REFERENCE TO RELATED APPLICATIONS

This application is a continuation of copending application Ser. No. 10/486,809 filed Apr. 12, 2004, entitled Device Based on Nitinol, A Process For Its Production, and Its Use, which is a 371 national phase filing of PCT/EP02/09017 filed Aug. 12, 2002, and claims priority to German Application No. 101 40 522.7, filed Aug. 17, 2001 and to German Application No. 102 02 467.7 filed Jan. 23, 2002, the entire disclosures of which are incorporated herein by reference.

The present invention relates to a device, comprising a substrate based essentially on nitinol and, arranged thereon at least partially, a covering or a coating based on at least one polyphosphazene derivative having the general formula (I), a process for its production, and the use of the device as an artificial implant, vascular or nonvascular stent, catheter, thrombolectomy or embolectomy catheter, fragmentation spindle or catheter, guide wire, filter, vascular connector, hernia patch, oral, dental or throat implant or urether.

The material nitinol is an intermetallic compound, mainly consisting of the metals nickel and titanium. After earlier deformation at a low temperature, nitinol has the peculiarity of assuming its original shape again after heating to a high temperature. This property is also known as "thermal shape memory". Moreover, nitinol has a second functional property, the "mechanical shape memory" or alternatively super-elasticity. The latter property in particular, the ability to tolerate elastic extensions up to 8% completely reversibly, has led to a large number of applications as implants and components for interventional treatment methods, such as, for example, stents, stent grafts, vascular connectors, filters, capture baskets and guide wires. Using insertion instruments, stents and filters are customarily brought to the position of the vessel at which they open up to the original shape. For insertion into the insertion system, the nitinol component is compressed in the cold at extensions up to approximately 8%. For instance, endovascular stents having a defined diameter are first processed, then compressed in the cold and brought to the position of the vessel at which they are to be placed by means of insertion instruments. At the desired position, the previously compressed stent opens up to its original shape due to the body heat and/or due to its elastic ability and supports the surrounding vessel. Owing to the shape which is already fixed during manufacture, an overextension of the vessel can be avoided.

The material nitinol per se has a very good body compatibility. In order to avoid from the start a "bleeding out" of nickel or nickel ions possibly occurring and in order to achieve a particularly uniform surface structure, various techniques were developed in order to seal the surface of an implant essentially manufactured from nitinol, such as, for example, a stent, and to provide it with a leakproof, nickel-impermeable layer. These processes of chemical aftertreatment customarily lead to a leakproof layer of titanium dioxide, through which nickel can hardly escape. These processes are known, inter alia, as electropolishing and are customary in different variants.

Although oxidic layers do not inevitably worsen the physical compatibility of implants, they yield a surface which only allows a low hemocompatibility to be expected and thus makes necessary the use of vitamin K antagonists, and other anticoagulants, such as acetyl-salicylic acid. This represents an additional stress for the affected patients.

Moreover, the process of electrochemical polishing cannot be employed everywhere. In areas or places in which electrochemical polishing cannot be used, such as, for example, in implants which consist of a combination of various materials and accordingly would dissolve these selectively during electrochemical polishing, natural oxide layers offer a poorer protection against the discharge of metal ions and accordingly a lower blood and physical compatibility.

A form of surface improvement to be additionally used would thus be desirable, such as, for example, a coating which makes leakproof the properties of a surface which is produced by electropolishing or in another way and is impermeable to metal ions, in particular nickel ions, with respect to the hemo- and biocompatibility and also further improves other properties, such as, in particular, the glidability, without damaging the leakproofness and isolating properties of such a surface.

From the prior art, an abundance of materials are known and investigated which are used for the production of such coatings. For instance, an expandable sheath of $\epsilon$-PTFE is disclosed in WO 98/56312, which can be used for the culturing of artificial vessels. Other materials for this use are cited in EP-A-0-810 845, in which, for example, polymers are mentioned which are described in U.S. Pat. No. 4,883,699 and U.S. Pat. No. 4,911,691. Further polymers for the purpose mentioned are, for example, hydrolyzed polyacrylonitrile (U.S. Pat. No. 4,480,642), hydro-philic polyethers (U.S. Pat. No. 4,798,876) and polyurethane diacrylates (U.S. Pat. No. 4,424,395). Furthermore, various hydrogels are known which can be employed as a coating for this purpose. The number of the potentially usable materials can be supplemented further by polyvinyl-pyrrolidone (PVP), polyvinyl alcohols (PVA), poly-ethylene oxide (PEO) and polyhydroxyethyl methacrylate p(HEMA). The use of a number of standard materials such as polyurethanes, polyethylenes and polypropylenes as possible materials is further described in the prior art. Likewise, mixtures of these materials with one another are known for the coating of implants. A number of further materials is moreover disclosed in EP-A-0-804 909.

The properties of these materials are different and it can be assumed therefrom that each of these materials has particular properties for certain applications in the coating of artificial implants and other medical devices. For instance, PVA is very readily soluble in liquids and is rapidly absorbed. Other materials have good blood compatibility. In turn, other materials are particularly readily stretchable. However, all materials exhibit disadvantages in certain areas. PVA, for example, does not show good blood compatibility. $\epsilon$-PTFE is very readily stretchable, for example, and also exhibits good blood compatibility, but this material is extremely difficult to handle and the production of such coatings necessitates a number of processing steps (cf. WO 96/00103). A surface obtained in such a way is also only temperature-stable within limits and becomes brittle in the cold, which in the specific case of the coating of nitinol leads at least to hairline cracks, at which thrombi can form. Moreover, the adhesion of such a coating is not particularly good. This becomes brittle during the cold treatment which is necessary and as a result of this detaches very easily, which in particular in the case of implants in endovascular systems can have considerable health sequelae. In the case of other materials, elastic properties which are important in virtually all cases for a coating of the type mentioned are only achieved by the addition of plasticizers. Plasticizers, however, decrease the blood and physical compatibility considerably. Further, a mobilization of the plasticizers can additionally lead to inflammatory reactions, reactions of the immune and anticoagulation system and thus to stress for the patients. Fundamentally, however, the majority of plastics and plastic mixtures "plasticized" in such a way become brittle in the cold and and lose their elasticity. As a result, in the case of such materials the danger is always present that on renewed expansion cracks form or the layer detaches.

Further known complications which can occur in the case of such a coating are connected with those of the degradation of some substances used for the coating and the degradation products resulting here. For instance, it is known that in the dissolution or the absorption and the decomposition of some of the coating substances known from the prior art inflammatory reactions can occur (van der Giessen, Circulation vol. 94, no. 7. 1996). This problem results either due to the in some cases imperfect compatibility of such coatings or else due to reaction to give decomposition products, which result in the decomposition of the substances mentioned. This lies in particular in the fact that the substances can in some cases only be applied in a not very controlled manner and thus are decomposed or degraded at different positions to a differently severe extent.

Further, for the problem-free handling of coated implants of this type the behavior toward bacteria, macrophages and proteins which deposit on the surfaces of the implants and devices plays a central role, since these deposits, in particular, can lead to inflammation and other problems during the growing-in of the implants. In particular, in the production of vascular implants, such as vascular and nonvascular stents, hernia patches, urethers, filters, vascular connectors, and implants in the oral, dental and throat region, the properties and peculiarities of the materials mentioned are a significant aspect. This is based on the fact that due to temperature effects during the processing of nitinol cracks produced are starting points for increased thrombus formation and other deposits such as proteins, macrophages, etc., which after implantation can become a risk for the patients.

The present invention is thus based on the object of making available a device based on nitinol suitable as an artificial implant, which is to be distinguished by high physical compatibility and a very good hemo-compatibility. Additionally, a device of this type should withstand the considerable temperature variations and mechanical stresses, such as, for example, elastic extensions of up to approximately 8%, which occur during the processing and use of the material nitinol, without a worsening of the property profile of the device, such as, for example, detachment or crack formation. This should in particular be achieved without the use of a plasticizer, since otherwise the physical compatibility of such an implant would be considerably decreased.

This object is achieved by the embodiments characterized in the claims. In particular, a device is made available comprising a substrate based essentially on nitinol and, arranged thereon at least partially, a covering or a coating based on at least one polymer having the following general formula (I),

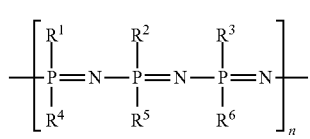
(I)

in which n is 2 to ∞, the radicals $R^1$ to $R^6$ are identical or different and are an alkoxy, alkyl-sulfonyl, dialkylamino or aryloxy radical or a hetero-cycloalkyl or heteroaryl radical having nitrogen as a hetero atom.

A further subject of the present invention is the use of the device according to the invention as an artificial implant, vascular or nonvascular stent, catheter, thrombolectomy or embolectomy catheter, fragmentation spindle or catheter, filter, vascular connector, hernia patch, oral, dental or throat implant, guide wire or urether, preferably as a vascular or nonvascular stent or as an oral, dental or throat implant.

Surprisingly, the device according to the invention exhibits a high physical compatibility and a very good hemocompatibility. Moreover, the device according to the invention shows essentially no adsorption of macrophages or colonization of bacteria. The polyphosphazene having the above formula (I) specifically selected in the context of the present invention for the coating of the substrate based on nitinol withstands in a particularly advantageous manner the in some cases extreme temperature variations and mechanical stresses in the course of the processing of the nitinol substrate without becoming brittle, detaching or tearing. As a result of the specifically selected polyphosphazene having the above formula (I), the surface properties of nitinol are permanently improved, since the specifically selected polyphosphazene derivative according to the general formula (I) is degraded neither hydrolytically nor enzymatically. Advantageously, the specifically selected polyphosphazene having the above formula (I) is elastic over a very wide temperature range, in particular at temperatures below the freezing point, without the use of plasticizers.

The degree of polymerization of the polymer according to the above formula (I) used for the coating of the nitinol substrate is 2 to ∞. A range for the degree of polymerization of from 20 to 200,000, more preferably of from 40 to 100,000, is preferred.

Preferably, at least one of the radicals $R^1$ to $R^6$ in the polymer used is an alkoxy radical which is substituted by at least one fluorine atom.

The alkyl radicals in the alkoxy, alkylsulfonyl and dialkylamino radicals are, for example, straight- or branched-chain alkyl radicals having 1 to 20 carbon atoms, where the alkyl radicals can be substituted, for example, by at least one halogen atom, such as a fluorine atom.

Examples of alkoxy radicals are methoxy, ethoxy, propoxy and butoxy groups, which can preferably be substituted by at least one fluorine atom. The 2,2,2-trifluoroethoxy group is particularly preferred. Examples of alkylsulfonyl radicals are methyl-, ethyl-, propyl- and butylsulfonyl groups. Examples of dialkylamino radicals are dimethyl-, diethyl-, dipropyl- and dibutylamino groups.

The aryl radical in the aryloxy radical is, for example, an aryl unit having one or more aromatic ring systems, where the aryl radical can be substituted, for example, by at least one alkyl radical defined above. Examples of aryloxy radicals are phenoxy and naphthoxy groups and derivatives thereof.

The heterocycloalkyl radical is, for example, a ring systems containing 3 to 7 atoms, where at least one ring atom is a nitrogen atom. The heterocycloalkyl radical can be substituted, for example, by at least one alkyl radical defined above. Examples of heterocycloalkyl radicals are piperidinyl, piperazinyl, pyrrolidinyl and morpholinyl groups and derivatives thereof. The heteroaryl radical is, for example, a compound having one or more aromatic ring systems, where at least one ring atom is a nitrogen atom. The heteroaryl radical can be substituted, for example, by at least one alkyl radical defined above. Examples of heteroaryl radicals are pyrrolyl, pyridinyl, pyridinolyl, isoquinolyl and quinolyl groups, and derivatives thereof.

In a preferred embodiment of the present invention, the polymer is poly[bis(trifluoroethoxy)phosphazene]. The polymer can also be a poly[bis(trifluoroethoxy)-phosphazene] labelled by $^{32}P$, $^{33}P$ or As or Sb isotopes.

As a volume material, the polymeric compound poly[bis(trifluoroethoxy)phosphazene] shows a good antithrombogenic action (cf. Tur, Investigations on the thrombus resistance of poly[bis(trifluoroethoxy)-phosphazene] and Hollemann Wiberg, "Stickstoff-verbindungen des Phosphors" [Nitrogen compounds of phosphorus], Textbook of inorganic chemistry, 666-669, 91st-100th edition, Walter de Gruyter Verlag, 1985, and Tur, Vinogradova, inter alia "Entwicklungstendenzen bei polymeranalogen Umsetzungen von Polyphosphazen" [Development tendencies in polymer-analogous reactions of polyphosphazene], Acta Polymerica 39, 424-429, no. 8, 1988. In DE 196 13 048 A1, the fluorinated form of polyphosphazenes was employed as a coating for the coating of artificial implants, heart valves expressly being mentioned. Such implants, however, are not produced from nitinol. Moreover, no disclosure is found in DE 196 13 048 A1 with respect to the aspect of the extreme temperature stresses in nitinol implants.

The devices according to the invention on the one hand have excellent mechanical and body-compatible properties and on the other hand a high resistance against inflammation-promoting organisms, such as, for example, macrophages. As a result of the coating of the nitinol surface with the specifically selected polyphosphazene having the above formula (I), on the one hand the hemo- and biocompatibility of the surface mentioned is improved, on the other hand in the application of the coating or of the covering the surface layer sealing the nitinol surface generated by electropolishing or other techniques is not damaged. Thus possible subsequent damage after implantation can be reduced.

In the context of the present invention, the substrate based on nitinol can be partially coated with a covering based on at least one polymer having the general formula (I). Customarily, however, it is preferred that the substrate is based on nitinol coated completely with a covering based on at least one polymer having the general formula (I).

In one embodiment of the present invention, the nitinol substrate, which coated thereon has a covering of the polyphosphazene polymer according to the formula (I), is present in the form of an at least partially pierced or perforated tube, such as is customary, for example, in the case of an endovascular implant, such as a stent.

The covering of at least one polyphosphazene polymer according to the formula (I) according to the present invention arranged or deposited on the nitinol substrate can further comprise one or more pharmaceutically active compounds, such as, for example, cytotoxic compounds, such as rapamycin, taxol, doxorubicin, platinum derivatives, 5-fluoracyl or antiinflammatory active compounds such as diclofenac or acetylsalicylic acid or other active compounds in a corresponding pharmaceutical preparation, preferably having delayed release or quantitatively controlled release over a relatively long period.

The covering of the device according to the invention has, for example, a thickness of approximately 1 nm to approximately 100 μm, preferably to approximately 500 nm and particularly preferably to approximately 100 nm.

In one embodiment of the artificial implant according to the invention, between the surface of the substrate and the covering constructed from the polyphosphazene derivative is arranged a layer which contains an adhesion promoter, i.e. adjacent to the coating based on at least one polymer having the general formula (I) is arranged an adhesion promoter layer.

The adhesion promoter or spacer preferably contains a polar end group. Examples of these are hydroxyl, carboxylate, aldehyde, amino or nitro groups. However, end groups based on an alkoxy, alkylsulfonyl, dialkylamino or aryloxy radical or a heterocycloalkyl or heteroaryl radical having nitrogen as a heteroatom can also be present, where these radicals can also be differently substituted, for example by halogen atoms, in particular fluorine.

In particular, the adhesion promoter can be, for example, an organosilicon compound, preferably an amino-terminated silane or a compound based on an aminosilane, an amino-terminated alkene, a nitro-terminated alkene, a nitro-terminated silane or an alkylphosphonic acid. As adhesion promoter, amino-propyltrimethoxysilane and aminopropyltriethoxysilane are particularly preferred.

The adhesion promoter in particular improves the adhesion of the covering to the surface of the nitinol substrate by coupling of the adhesion promoter to the nitinol surface, for example by means of ionic and/or covalent bonds, and further coupling to the described polymer of the formula (I) of the covering, for example by means of ionic and/or covalent bonds.

A further subject of the present invention relates to the production of the device according to the invention, comprising the steps:
(a) making available of a substrate based on nitinol,
(b) exposure of the nitinol surface to a plasma treatment,
(c) optionally hydroxylation of the surface treated in step (b) and application of an adhesion promoter and
(d) coating of the substrate with at least one polymer of the abovementioned formula (I).

The substrate based on nitinol can be made available in step (a), for example, in the form of an at least partially pierced or perforated tube. The substrate essentially comprises nitinol as the material forming the substrate. The substrate based on nitinol can in the course of this already be subjected to an electropolishing or other treatment for the production of a surface which is leakproof and impermeable to nickel ions.

In step (b) of the process according to the invention, a plasma treatment of the nitinol surface takes place, the plasma preferably being an air or oxygen plasma. By means of the plasma treatment, an ultrathin, leakproof $TiO_2$ layer is produced on the substrate based essentially on nitinol. Other plasma gases such as, for example, argon can also be employed. The plasma gases employed can further optionally contain one or more additives customary in such a process step, such as, for example, allyl, vinylbenzene, etc. In step (b) of the process according to the invention, an activation and cleaning of the nitinol surface by means of the plasma treatment takes place, whereby a complete and uniform oxidation and activation of the surface is brought about. At the same time, impurities or foreign bodies present are oxidized and the surface is cleaned. In this connection, it is to be mentioned that the activation and coating of the surface, as described in DE 196 13 048, removes a surface produced by electropolishing and thus allows the escape of nickel or nickel ions. The procedure described in DE 196 13 048 is therefore unsuitable for the coating of nitinol implants or devices and leads to implants whose use brings about potential harm to the patient by the elution of nickel or nickel ions. Furthermore, as a result of the use of sulfuric acid described in DE 196 13 048 the formation of compounds of the type $TiO(SO_4)$ occurs, which dissolves and thus damages and destroys the $TiO_2$ surface generated by the surface treatment.

Subsequently, in step (c) a hydroxylation of the nitinol surface, for example by water, is optionally carried out and an adhesion promoter, preferably amino-propyltrimethoxysilane (APTMS) or aminopropyltriethoxy-silane, is applied to the surface and crosslinked.

A solution which contains at least one compound of the general formula (I) in a concentration of 0.1 to 99% by weight is then applied to this surface in step (d), customarily by spraying or dipping. As possible solvents, ethyl acetate, acetone, THF, toluene or xylenes can be used here. However, the choice of the solvents or solvent mixtures is not restricted to the solvents mentioned.

The evaporation of the solvent can proceed without further measures. Customarily, the concentration of the solvent vapor above the substrate, the pressure and the temperature is controlled. At the beginning of the first drying phase, an atmosphere saturated with the solvent vapor is customarily established above the coated substrate, the concentration of the solvent vapor subsequently being slowly reduced over a number of hours. The temperature can vary here from −30° C. to +90° C. During the first drying phase, the pressure can run through a ramp from normal pressure to water jet vacuum (20 torr). After the first drying phase, the coated substrate is then dried further for a certain time in an oil pump vacuum (0.1 torr).

The device coated with the dried polymer of the compound (I) based on nitinol can then be directly further used after appropriate sterilization and further processed in the cold, i.e. compressed. Depending on the concentration of the solution of the polymer compound (I) and the conditions during the first drying phase, various layer thicknesses of from 0.1 nm to 300 μm or thicker, preferably in the range from 500 nm to 30 μm, and particularly preferably around 100 nm, can be produced.

The structuring of the polymer coating is subject to no specific restriction. Thus structures of the order of magnitude of nanometers, micrometers or even larger or smaller, preferably in the range from 10 nm to 100 μm, can be produced. Furthermore, all structures can be produced and used which can be generated photolithographically or using electron beams, X-rays or laser beams or by means of other techniques.

A microstructuring of the coating can also be obtained by means of direct "writing" on a film produced beforehand based on at least one polyphosphazene derivative according to the above formula (I) by means of laser beams, electron beams or X-rays or else by "melt structuring", where a thin wire is brought to the melting temperature of the polymer, which then melts the desired structure into the coating by direct contact. Particular advantages can be achieved by a structuring of this type in that structures are imprinted in the film which particularly favorably arrange the flow behavior of liquids (e.g. sharkskin or lotus effect).

The invention claimed is:

1. A device comprising:
a substrate comprising an intermetallic compound of nickel and titanium;
a $TiO_2$ layer disposed on the substrate and produced by electropolishing and plasma treatment of the substrate resulting in a uniform oxidation of the surface;
an adhesion promoter disposed above the substrate; and
a coating, disposed on the adhesion promoter, comprising a polymer having the general formula (I),

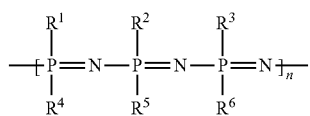

wherein n is 2 to ∞, the radicals $R^1$ to $R^6$ are identical or different and are selected from an alkoxy, alkyl sulfonyl, dialkylamino, aryloxy radical, a heterocycloalkyl radical having nitrogen as a heteroatom, and a heteroaryl radical having nitrogen as a heteroatom.

2. The device of claim 1, wherein at least one of the radicals $R^1$ to $R^6$ is an alkoxy radical which is substituted by at least one fluorine atom.

3. The device of claim 1, wherein the polymer is poly[bis (trifluoroethoxy)phosphazene].

4. The device of claim 1, wherein the adhesion promoter is a compound containing a polar end group.

5. The device claim 1, wherein the adhesion promoter is an organosilicon compound.

6. The device of claim 5, wherein the organosilicon compound is aminopropyltrimethoxysilane.

7. The device of claim 1, wherein the substrate is formed as a stent.

8. The device of claim 1, wherein the coating is microstructured.

9. The device of claim 1, wherein the device is selected from the group consisting of an artificial implant, a vascular stent, a non-vascular stent, a catheter, a thrombolectomy catheter, an embolectomy catheter, a fragmentation spindle, a fragmentation catheter, a filter, a vascular connector, a hernia patch, an oral implant, a dental implant, a throat implant, a guide wire, and a ureter.

10. The device of claim 1, wherein the coating further comprises one or more pharmaceutically active compounds released in a controlled manner over an extended period.

11. The device of claim 1, wherein the coating has a thickness ranging from approximately 1 nm to approximately 100 μm.

12. The device of claim 1, wherein the polymer is poly[bis (trifluoroethoxy)phosphazene], the adhesion promoter comprises an aminopropyl-trimethoxysilane, the substrate is formed as at least a partially perforated tube, and the coating is micro-structured.

13. The device of claim 1, wherein the coating has a thickness ranging from approximately 0.1 nm to approximately 300 μm.

14. The device of claim 1, wherein the $TiO_2$ layer remains as formed beneath the adhesion promoter and coating.

15. The device of claim 1, wherein the $TiO_2$ layer is produced by electropolishing followed by plasma treatment.

16. A process for producing a device comprising:
providing a substrate comprising an intermetallic compound of nickel and titanium;
exposing the substrate to electropolishing and a plasma treatment resulting in a uniform oxidation of the surface of the substrate to form a $TiO_2$ layer above the substrate;
disposing an adhesion promoter; and
coating the adhesion promoter with at least one polymer according to the formula (I),

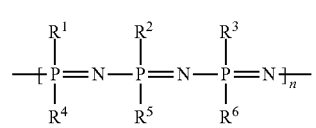

wherein n is 2 to 00, the radicals $R^1$ to $R^6$ are identical or different and are selected from an alkoxy, alkyl sulfonyl, dialkylamino, aryloxy radical, a heterocycloalkyl radical having nitrogen as a heteroatom, and a heteroaryl radical having nitrogen as a heteroatom.

17. The process of claim 11, wherein exposing the substrate to the plasma treatment includes utilizing air, argon, or oxygen plasma.

18. The process of claim 16, further comprising microstructuring a surface of the polymer coating by exposing to a laser beam, an electron beam or X-ray radiation, and/or a heated wire.

19. The process of claim 16, further comprising hydroxylating the substrate subsequent to the plasma treatment and before disposing an adhesion promoter.

20. The process of claim 16, wherein exposing the substrate to the plasma treatment includes utilizing air, argon, or oxygen plasma.

21. The process of claim 16 further comprising microstructuring the polymer coating, by exposing to a laser beam, an electron beam or X-ray radiation, and/or a heated wire.

22. The process of claim 16, wherein coating the substrate with at least one polymer further comprises spraying or dipping in a polymer solution containing at least one compound of the general formula (I) at a concentration of about 0.1 to 99% by weight.

23. The process of claim 16, wherein the coating has a thickness ranging from approximately 0.1 nm to approximately 300 μm.

24. The process of claim 16, wherein the coating has a thickness ranging from approximately 1 nm to approximately 100 μm.

25. The process of claim 16, wherein the $TiO_2$ layer remains as formed through the coating step.

26. The process of claim 16, wherein the $TiO_2$ layer is produced by electropolishing followed by plasma treatment.

* * * * *